(12) United States Patent
Barta et al.

(10) Patent No.: US 6,949,575 B2
(45) Date of Patent: Sep. 27, 2005

(54) METHOD OF INHIBITING AMYLOID PROTEIN AGGREGATION AND IMAGING AMYLOID DEPOSITS USING AMINOINDANE DERIVATIVES

(75) Inventors: Nancy Sue Barta, Brighton, MI (US); Christopher Franklin Bigge, Ann Arbor, MI (US)

(73) Assignee: Pfizer Inc., New York, NY (US)

(*) Notice: Subject to any disclaimer, the term of this patent is extended or adjusted under 35 U.S.C. 154(b) by 106 days.

(21) Appl. No.: 10/275,351

(22) PCT Filed: Apr. 25, 2001

(86) PCT No.: PCT/US01/13254

§ 371 (c)(1),
(2), (4) Date: Nov. 4, 2002

(87) PCT Pub. No.: WO01/83425

PCT Pub. Date: Nov. 8, 2001

(65) Prior Publication Data

US 2003/0220382 A1 Nov. 27, 2003

Related U.S. Application Data

(60) Provisional application No. 60/201,996, filed on May 4, 2000.

(51) Int. Cl.[7] .................. A01N 43/64; A01N 37/12; A01N 37/44; A61K 31/41; A61K 31/24
(52) U.S. Cl. .................. 514/381; 514/535; 514/564; 514/567; 514/657; 548/253; 548/254; 560/43; 562/454; 562/457; 564/428
(58) Field of Search .................. 514/381, 535, 514/564, 567, 657; 548/253, 254; 560/43; 562/454, 457; 564/428

(56) References Cited

U.S. PATENT DOCUMENTS

| | | | |
|---|---|---|---|
| 4,816,456 A | | 3/1989 | Summers .................. 514/255 |
| 5,006,561 A | * | 4/1991 | Arrowsmith et al. ....... 514/605 |
| 5,523,314 A | | 6/1996 | Bue-Valleskey et al. .... 514/369 |
| 5,658,904 A | | 8/1997 | Ono et al. .............. 514/237.2 |
| 5,716,975 A | | 2/1998 | Bue-Valleskey et al. .... 514/369 |
| 6,001,331 A | | 12/1999 | Caprathe et al. ............. 424/9.1 |

FOREIGN PATENT DOCUMENTS

| | | | |
|---|---|---|---|
| CA | 2335560 | * | 1/1999 |
| EP | 0535496 | | 9/1992 |
| EP | 0538134 | | 10/1992 |

OTHER PUBLICATIONS

Nakagawa et al, "Caspase–12 mediates endoplasmic reticulum–specific apoptosis and cytotoxicity by amyloid–beta" Nature, vo 403, pp. 98–103 (Jan. 6, 2000).*
Thal, "Trials to slow progression and prevent disease onset" J. Neural Transm. [Suppl] vol. 59, pp. 243–249 (2000).*
Reichman, W. E., "Alzheimer's Disease: Clinical Treatment Options" vol. 6(22) Sup., pp. S1125–S1138 (Dec. 2000).*
Schenk et al, "Immunization with amyloid–beta attenuates Alzheimer–disease–like pathology in the PDAPP mouse" Nature, vol. 400, pp. 173–177 (Jul. 8, 1999).*
Lue et al, "Soluble Amyloid beta Peptide Concentration as a Predictor of Synaptic Change in Alzheimer's Disease" American Journal of Pathology, vol. 155(3), pp. 853–.*
Mclean et al, "Soluble Pool of A–beta Amyloid as a Determinant of Severity of Neurodegeneration in Alzheimer's Disease" Annals of Neurology, vol. 46(6), pp. 860–866 (Dec. 1999).*
Yan et al, "Membrane–anchored aspartyl protease with Alzheimer's disease beta–secretase activity" Nature, vol. 402, pp. 533 537 (Dec. 2, 1999).*
Bort et al, "Comparative metabolism of the nonsteroidal antiiinflammatory drug aceclofenac, in the rat, monkey and human." Drug metabolism and disposition: biological fate of chemicals, vol. 24(9), pp. 969–975 (1996).*
Al–Dabbagh and Smith, "Species differences in oxidative drug metabolism: some basic considerations." Archives of toxicology. Supplement. Archiv fur Toxikologie. supplement, vol. 7, pp. 219–231 (1984).*
Thal, L.J. "Trials to slow progression and prevent disease onset" J. Neural Transmission, Supplementum, vol. 59, pp. 243–249 (2000).*
Reichman, W.E. "Alzheimer's Disease: Clinical Treatment Options" Am. J. Managed Care, vol. 6, pp. S1133–S1138 (Dec. 2000).*
Klein, William, "A.beta. toxicity in Alzheimer's disease: globular oligomers (ADDLs) as new vaccine and drug targets" Neurochemistry International, vol. 41, pp. 345–352 (2002).*
Reichman, W. E. "Current pharmacologic options for patients with Alzheimer's disease" Annals of General Hospital Psychiatry, vol. 2:1, online article, 14 pages (Jan. 2003).*
PCT International Search Report PCT/US01/13254.

* cited by examiner

Primary Examiner—James O. Wilson
Assistant Examiner—Zachary C. Tucker
(74) Attorney, Agent, or Firm—P. C. Richardson; L. B. Ling; J. A. Jubinsky

(57) ABSTRACT

The present invention provides compounds of Formula (I) and a method of treating Alzheimer's disease using a compound of Formula (I), wherein: $R^1$ and $R^2$ include alkyl and phenylalkyl; $R^3$ is hydrogen or alkyl; and $R_4$ and $R_5$ include alkyl, alkoxy, carboxyl, alkoxycarbonyl, and nitro. Also provided is a method of inhibiting the aggregation of amyloid proteins using a compound of Formula (I)

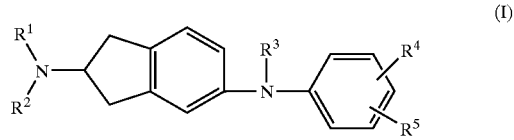

and a method of imaging amyloid deposits using compounds of Formula (I).

12 Claims, No Drawings

METHOD OF INHIBITING AMYLOID PROTEIN AGGREGATION AND IMAGING AMYLOID DEPOSITS USING AMINOINDANE DERIVATIVES

This application is a 371 application of PCT/US01/13254 filed Apr. 25, 2001, which claims the benefit of priority to U.S. provisional application Ser. No. 60/201,996 filed May 4, 2000.

FIELD OF THE INVENTION

This invention relates to a method of inhibiting amyloid protein aggregation and imaging amyloid deposits. More particularly, this invention relates to a method of inhibiting amyloid protein aggregation in order to treat Alzheimer's disease using aminoindane derivatives.

BACKGROUND OF THE INVENTION

Amyloidosis is a condition characterized by the accumulation of various insoluble, fibrillar proteins in the tissues of a patient. The fibrillar proteins that comprise the accumulations or deposits are called amyloid proteins. While the particular proteins or peptides found in the deposits vary, the presence of fibrillar morphology and a large amount of β-sheet secondary structure is common to many types of amyloids. An amyloid deposit is formed by the aggregation of amyloid proteins, followed by the further combination of aggregates and/or amyloid proteins.

The presence of amyloid deposits has been shown in various diseases, each with its particular associated protein, such as Mediterranean fever, Muckle-Wells syndrome, idiopathic myeloma, amyloid polyneuropathy, amyloid cardiomyopathy, systemic senile amyloidosis, amyloid polyneuropathy, hereditary cerebral hemorrhage with amyloidosis, Alzheimer's disease, Down syndrome, Scrapie, Creutzfeldt-Jacob disease, Kuru, Gerstrnann-Straussler-Scheinker syndrome, medullary carcinoma of the thyroid, Isolated atrial amyloid, $\beta_2$-microglobulin amyloid in dialysis patients, inclusion body myositis, $\beta_2$-amyloid deposits in muscle wasting disease, Sickle Cell Anemia, Parkinson's disease, and Islets of Langerhans diabetes type 2 insulinoma.

A simple, noninvasive method for detecting and quantitating amyloid deposits in a patient has been eagerly sought. Presently, detection of amyloid deposits involves histological analysis of biopsy or autopsy materials. Both methods have major drawbacks. For example, an autopsy can only be used for a postmortem diagnosis.

The direct imaging of amyloid deposits in vivo is difficult, as the deposits have many of the same physical properties (i.e., density and water content) as normal tissues. Attempts to image amyloid deposits directly using magnetic resonance imaging (MRI) and computer-assisted tomography (CAT) have been disappointing and have detected amyloid deposits only under certain favorable conditions. In addition, efforts to label amyloid deposits with antibodies, serum amyloid P protein, or other probe molecules has provided some selectivity on the periphery of tissues, but has provided for poor imaging of tissue interiors.

Thus, it would be useful to have a noninvasive technique for imaging and quantitating amyloid deposits in a patient. In addition, it would be useful to have compounds that inhibit the aggregation of amyloid proteins to form amyloid deposits.

One of the most devastating diseases associated with amyloid deposits is Alzheimer's disease. Alzheimer's disease is a degenerative brain disorder characterized clinically by progressive loss of memory, cognition, reasoning, judgement, and emotional stability that gradually leads to mental deterioration and ultimately death. Because Alzheimer's disease and related degenerative brain disorders are a major medical issue for an increasingly aging population, the need for new treatments and methods for diagnosing the disorders are needed.

Several classes of compounds have been shown to have activity against Alzheimer's disease. The only two agents currently approved for clinical treatment of Alzheimer's disease are the acetylcholinesterase inhibitors tacrine and donepezil (see U.S. Pat. No. 4,816,456). U.S. Pat. Nos. 5,716,975 and 5,523,314 relate to rhodanine derivatives useful as hypoglycemic agents and for treating Alzheimer's disease.

The present invention provides a group of aminoindanyl analogs that are inhibitors of amyloid aggregation and are thus useful for treating Alzheimer's disease. The compounds are also useful as imaging agents because of their ability to selectively bind to amyloid proteins.

SUMMARY OF THE INVENTION

The present invention provides compounds of the Formula I

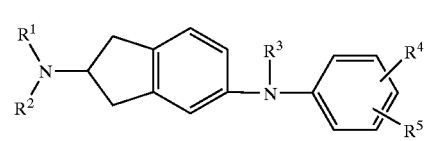

wherein:

$R^1$ and $R^2$ independently are hydrogen, $C_1-C_8$ alkyl, $C_2-C_8$ alkenyl, $C_2-C_8$ alkynyl, $(CH_2)_n$ phenyl or $(CH_2)_n$ substituted phenyl, provided that one of $R^1$ and $R^2$ is other than hydrogen;

$R^4$ and $R^5$ independently are hydrogen, halo, $C_1-C_8$ alkyl, $C_2-C_8$ alkenyl, $C_2-C_8$ alkynyl, $(CH_2)_n$ phenyl, $(CH_2)_n$ substituted phenyl, $NO_2$, CN, $CF_3$, $C_1-C_8$ alkoxy, $CO_2R^6$, tetrazolyl, $NH(C_1-C_8$ alkyl), $N(C_1-C_8$ alkyl)$_2$, or $SO_2R^6$;

$R^3$ is hydrogen or $C_1-C_8$ alkyl;

$R^6$ is hydrogen, $C_1-C_8$ alkyl, or $(CH_2)_n$phenyl or $(CH_2)_n$ substituted phenyl;

n is an integer from 0 to 4 inclusive;

or a pharmaceutically acceptable salt, ester, amide, or prodrug thereof.

Preferred compounds have Formula I wherein one of $R^1$ and $R^2$ is $(CH_2)_n$phenyl or $(CH_2)_n$ substituted phenyl, and $R^5$ is $CO_2R^6$, tetrazolyl, or $SO_2 R^6$, and $R^6$ is hydrogen.

A preferred group of compounds have Formula II

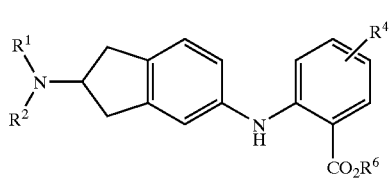

where $R^1$, $R^2$, $R^4$, and $R^6$ are as defined above.

Another preferred group of compounds have Formula III

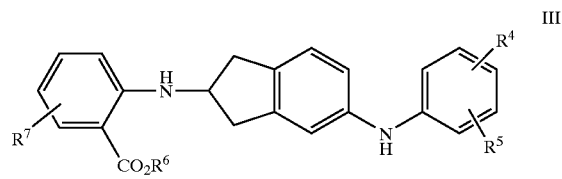

where in $R^4$, $R^5$, and $R^6$ are as defined above, and $R^7$ is hydrogen, halo, $NO_2$, CN, $C_1$–$C_8$ alkyl, $C_1$–$C_8$ alkoxy, $CF_3$, $NH_2$, $NH(C_1$–$C_8$alkyl), or $N(C_1$–$C_8$alkyl)$_2$.

A further embodiment of this invention is a pharmaceutical composition comprising a compound of Formula I together with a carrier, excipient, or diluent therefor.

Another embodiment of this invention is a method for inhibiting amyloid aggregation in a mammal comprising administering an effective amount of a compound of Formula I. A further method provided is a method of treating Alzheimer's disease and central and/or peripheral amyloidosis syndromes in mammals comprising administering an effective amount of a compound of Formula I.

Also provided is a method of imaging amyloid deposits, the method comprising the steps of:

a. introducing into a patient a detectable quantity of a labeled compound of Formula I;
b. allowing sufficient time for the labeled compound to become associated with amyloid deposits; and
c. detecting the labeled compound associated with the amyloid deposits.

In a preferred embodiment of the method, the patient has or is suspected to have Alzheimer's disease.

In another preferred embodiment, the labeled compound is a radiolabeled compound.

In another preferred embodiment, the labeled compound is detected using MRI.

Also provided is a pharmaceutical composition comprising a compound of Formula I.

DETAILED DESCRIPTION OF THE INVENTION

The term "alkyl" means a straight or branched chain hydrocarbon. Representative examples of alkyl groups are methyl, ethyl, propyl, isopropyl, isobutyl, butyl, tert-butyl, sec-butyl, pentyl, and hexyl.

Preferred alkyl groups are $C_1$–$C_8$ alkyl.

"Alkenyl" means a carbon chain having one or two points of unsaturation in the form of double bonds. Examples include ethenyl, prop-2-enyl, and hex-2,4-dienyl.

"Alkynyl" means a carbon chain having one or two triple bonds, for example, 2-butynyl, octa-3,5-diynyl, and the like.

The term "alkoxy" means an alkyl group such as $C_1$–$C_8$ alkyl attached to an oxygen atom. Representative examples of alkoxy groups include methoxy, ethoxy, tert-butoxy, propoxy, and isobutoxy.

The term "halogen" includes chlorine, fluorine, bromine, and iodine.

The foregoing alkyl, alkenyl, alkynyl, and alkoxy groups can be substituted.

The term "substituted" means that one or more hydrogen atoms in a molecule has been replaced with another atom or group of atoms. For example, substituents include halogen, —OH, —$CF_3$, —$NO_2$, —$NH_2$, —$NH(C_1$–$C_8$alkyl), —$N(C_1$–$C_8$alkyl)$_2$, $C_1$–$C_8$ alkyl, —$OC_1$–$C_8$ alkyl, —CN, —$CF_3$, —$CO_2H$, —$CO_2C_1$–$C_8$ alkyl, $SO_2H$, and $SO_2C_1$–$C_8$ alkyl.

The term "substituted phenyl" means a phenyl ring in which from 1 to 4 hydrogen atoms have been independently replaced with a substituent, preferably one selected from the list above. Examples of substituted phenyl include 2,6-dichlorophenyl, 2-methoxycarbonylphenyl, 3-cyanophenyl, 2,3,4,5-tetrafluorophenyl, 3-aminophenyl, 2-hydroxyphenyl, and the like.

The symbol "-" means a covalent bond.

The term "pharmaceutically acceptable salt, ester, amide, and prodrug" as used herein refers to those carboxylate salts, amino acid addition salts, esters, amides, and prodrugs of the compounds of the present invention which are, within the scope of sound medical judgement, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively nontoxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laureate, borate, benzoate, lactate, phosphate, tosylate, citrate, maleate, fumarate, succinate, tartrate, naphthylate mesylate, glucoheptonate, lactiobionate and laurylsulphonate salts, and the like. These may include cations based on the alkali and alkaline earth metals, such as sodium, lithium, potassium, calcium, magnesium, and the like, as well as, nontoxic ammonium, quaternary ammonium and amine cations including, but not limited to ammonium, tetramethylammonium, tetraethylammonium, methylamine, dimethylamine, trimethylamine, triethylamine, ethylamine, and the like. (See, for example, Berge S. M., et al., Pharmaceutical Salts, *J. Pharm. Sci.,* 66:1-19 (1977) which is incorporated herein by reference.)

Examples of pharmaceutically acceptable, nontoxic esters of the compounds of this invention include $C_1$–$C_8$ alkyl esters wherein the alkyl group is a straight or branched chain. Acceptable esters also include $C_5$–$C_7$ cycloalkyl esters as well as arylalkyl esters such as, but not limited to benzyl. $C_1$–$C_4$ alkyl esters are preferred. Esters of the compounds of the present invention may be prepared according to conventional methods.

Examples of pharmaceutically acceptable, nontoxic amides of the compounds of this invention include amides derived from ammonia, primary $C_1$–$C_8$ alkyl amines, and secondary $C_1$–$C_8$ dialkyl amines wherein the alkyl groups are straight or branched chain. In the case of secondary amines, the amine may also be in the form of a 5- or 6-membered heterocycle containing one nitrogen atom. Amides derived from ammonia, $C_1$–$C_3$ alkyl primary amides, and $C_1$–$C_2$ dialkyl secondary amides are preferred. Amides of the compounds of the invention may be prepared according to conventional methods.

The term "prodrug" refers to compounds that are rapidly transformed in vivo to yield the parent compound of the above formulas, for example, by hydrolysis in blood. A thorough discussion is provided in T. Higuchi and V. Stella, *Pro-drugs as Novel Delivery Systems,* Vol. 14 of the A.C.S. Symposium Series, and in *Bioreversible Carriers in Drug Design,* ed. Edward B. Roche, American Pharmaceutical Association and Pergamon Press, 1987, both of which are incorporated herein by reference.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

The compounds of the present invention can exist in different stereoisometric forms by virtue of the presence of asymmetric centers in the compounds. It is contemplated that all stereoisometric forms of the compounds, as well as mixture thereof, including racemic mixtures, form part of this invention.

In the first step of the present method of imaging, a labeled compound of Formula I is introduced into a tissue or a patient in a detectable quantity. The compound is typically part of a pharmaceutical composition and is administered to the tissue or the patient by methods well-known to those skilled in the art.

In the methods of the present invention, a compound can be administered either orally, rectally, parenterally (intravenous, by intramuscularly or subcutaneously), intracisternally, intravaginally, intraperitoneally, intravesically, locally (powders, ointments or drops), or as a buccal or nasal spray.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents, or vehicles include water, ethanol, polyols (propyleneglycol, polyethyleneglycol, glycerol, and the like), suitable mixtures thereof, vegetable oils (such as olive oil), and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid; (b) binders, as for example, carboxymethylcellulose, alignates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates and sodium carbonate; (e) solution retarders, as for example paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft- and hard-filled gelatin capsules using such excipients as lactose or milk sugar, as well as high molecular weight polyethyleneglycols, and the like.

Solid dosage forms such as tablets, dragees, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present invention with suitable nonirritating excipients or carriers such as cocoa butter, polyethyleneglycol, or a suppository wax, which are solid at ordinary temperatures but liquid at body temperature and therefore, melt in the rectum or vaginal cavity and release the active component.

Dosage forms for topical administration of a compound of this invention include ointments, powders, sprays, and inhalants. The active component is admixed under sterile conditions with a physiologically acceptable carrier and any preservatives, buffers or propellants as may be required. Ophthalmic formulations, eye ointments, powders, and solutions are also contemplated as being within the scope of this invention.

In a preferred embodiment of the invention, the labeled compound is introduced into a patient in a detectable quantity and after sufficient time has passed for the compound to become associated with amyloid deposits, the labeled compound is detected noninvasively inside the patient. In another embodiment of the invention, a labeled compound of Formula I is introduced into a patient, sufficient time is allowed for the compound to become associated with amyloid deposits, and then a sample of tissue from the patient is removed and the labeled compound in the tissue is detected apart from the patient. In a third embodiment of the invention, a tissue sample is removed from a patient and a labeled compound of Formula I is introduced into the tissue sample. After a sufficient amount of time for the compound to become bound to amyloid deposits, the compound is detected.

The administration of the labeled compound to a patient can be by a general or local administration route. For example, the labeled compound may be administered to the patient such that it is delivered throughout the body. Alternatively, the labeled compound can be administered to a specific organ or tissue of interest. For example, it is desirable to locate and quantitate amyloid deposits in the brain in order to diagnose or track the progress of Alzheimer's disease in a patient.

The term "tissue" means a part of a patient's body. Examples of tissues include the brain, heart, liver, blood vessels, and arteries. A detectable quantity is a quantity of labeled compound necessary to be detected by the detection method chosen. The amount of a labeled compound to be introduced into a patient in order to provide for detection can readily be determined by those skilled in the art. For example, increasing amounts of the labeled compound can be given to a patient until the compound is detected by the detection method of choice. A label is introduced into the compounds to provide for detection of the compounds.

The term "patient" means humans and other animals. Those skilled in the art are also familiar with determining the amount of time sufficient for a compound to become associated with amyloid deposits. The amount of time necessary can easily be determined by introducing a detectable amount of a labeled compound of Formula I into a patient and then detecting the labeled compound at various times after administration.

The term "associated" means a chemical interaction between the labeled compound and the amyloid deposit. Examples of associations include covalent bonds, ionic bonds, hydrophilic-hydrophilic interactions, hydrophobic-hydrophobic interactions, and complexes.

Those skilled in the art are familiar with the various ways to detect labeled compounds. For example, MRI, positron emission tomography (PET), or single photon emission computed tomography (SPECT) can be used to detect radio-labeled compounds. The label that is introduced into the compound will depend on the detection method desired. For example, if PET is selected as a detection method, the compound must possess a positron-emitting atom, such as $^{11}$C or $^{18}$F.

Another example of a suitable label in a compound of Formula I is an atom such as $^{13}$C, $^{15}$N, or $^{19}$F which can be detected using MRI which is also sometimes called nuclear magnetic resonance (NMR). In addition, the labeled compounds of Formula I may also be detected by MRI using paramagnetic contrast agents.

Another example of detection is electron paramagnetic resonance (EPR). In this case, EPR probes which are well-known in the art, such as nitroxides, can be used.

The imaging of amyloid deposits can also be carried out quantitatively so that the amount of amyloid deposits can be determined.

The present invention also provides a method of inhibiting the aggregation of amyloid proteins to form amyloid deposits, by administering to a patient in need of inhibition of the aggregation of amyloid protein an amyloid protein inhibiting amount of a compound of Formula I. Those skilled in the art are readily able to determine an amyloid inhibiting amount by simply administering a compound of Formula I to a patient in increasing amounts until the growth of amyloid deposits is decreased or stopped. The rate of growth can be assessed using imaging or by taking a tissue sample from a patient and observing the amyloid deposits therein.

A patient in need of inhibition of the aggregation of amyloid proteins is a patient having a central or peripheral disease or condition in which amyloid proteins aggregate. Examples of such diseases and conditions include Mediterranean fever, Muckle-Wells syndrome, idiopathetic myeloma, amyloid polyneuropathy, amyloid cardiomyopathy, systemic senile amyloidosis, amyloid polyneuropathy, hereditary cerebral hemorrhage with amyloidosis, Alzheimer's disease, Down syndrome, Scrapie, Creutzfeldt-Jacob disease, Kuru, Gerstmann-Straussler-Scheinker syndrome, medullary carcinoma of the thyroid, Isolated atrial amyloid, $\beta_2$-microglobulin amyloid in dialysis patients, inclusion body myositis, $\beta_2$-amyloid deposits in muscle wasting disease, Sickle Cell Anemia, Parkinson's disease, and Islets of Langerhans diabetes type 2 insulinoma.

Also provided by the present invention are compounds of Formula I wherein one or more atom in the compound has been replaced with a radioisotope. The radioisotope can be any radioisotope. However, $^{3}$H, $^{123}$I, $^{1}$I, $^{131}$I, $^{11}$C, and $^{18}$F are preferred. Those skilled in the art are familiar with the procedure used to introduce a radioisotope into a compound. For example, compounds of Formula I are made where a $^{12}$C atom is replaced by a $^{13}$C atom.

The compounds of the present invention can be administered to a patient at dosage levels in the range of about 0.1 to about 1,000 mg per day, which are "effective amounts" for inhibiting amyloid formation and treating the above mentioned diseases, especially Alzheimer's disease. For a normal human adult having a body weight of about 70 kg, a dosage in the range of about 0.01 to about 100 mg per kilogram of body weight per day is sufficient. The specific dosage used, however, can vary. For example, the dosage can depend on a number of factors including the requirements of the patient, the severity of the condition being treated, and the pharmacological activity of the compound being used. The determination of optimum dosages for a particular patient is well-known to those skilled in the art.

The compounds of Formula I can be prepared by any of several processes, utilizing readily available starting materials and methods well-known in organic chemistry. Scheme 1 below illustrates a typical method for making starting materials and the final products of Formula I. The invention compounds are generally prepared by reacting an amino indane with a phenyl halide such as a phenyl iodide or phenyl bromide.

Scheme 1 starts with a 2-amino-5-nitro-indane, which can be prepared by reacting 2-amino-indane with nitric acid and sulfuric acid, generally in a solvent such as trifluoroacetic acid.

The 2-amino-5-nitro-indane is readily reduced to the corresponding 2,5-diaminoindane, for instance by hydrogenation in the presence of a catalyst such as Raney nickel. The 5-amino group is then readily phenylated by reaction with a R⁴ phenyl compound

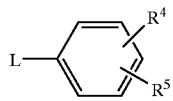

bearing a good leaving group L, for example where L is halo such as iodo. The reaction is carried out under standard palladium-mediated coupling conditions, such as in an organic solvent (e.g., toluene) and in the presence of a mild base (e.g., cesium carbonate). The product, a 2-amino-5-phenylaminoindane, is further alkylated or phenylated at the 2-amino position, again utilizing standard alkylation methods.

Schemes 2, 3, and 4 illustrate the initial alkylation or phenylation of the 2-amino group of a 2-amino-5-nitro-indane, followed by reduction of the nitro group and phenylation of the 5-amino group. All of these reactions are carried out under standard conditions, for example in an unreactive organic solvent, in the presence of a mild base, and generally at an elevated temperature of about 60° C. to about 150° C. The products are readily isolated by simply removing the reaction solvent, for example by evaporation under reduced pressure, and they can be purified if desired by standard methods such as chromatography, crystallization, distillation, and the like.

Scheme 1

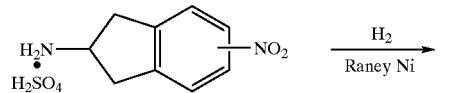

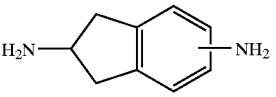

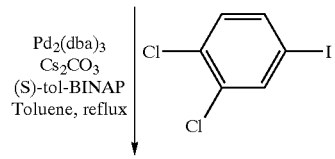

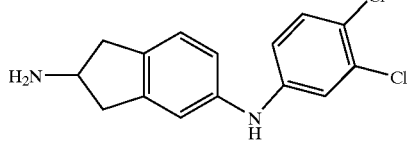

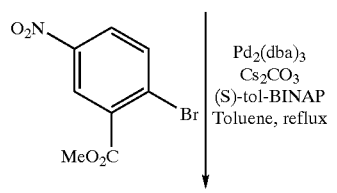

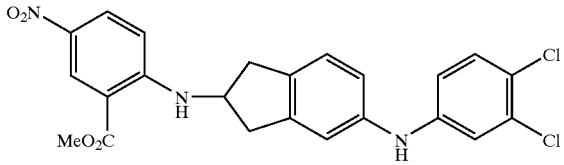

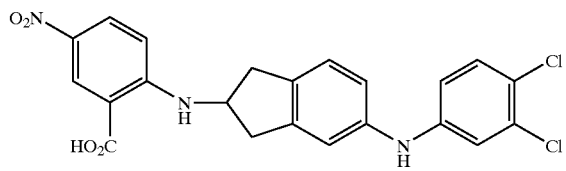

Scheme 2

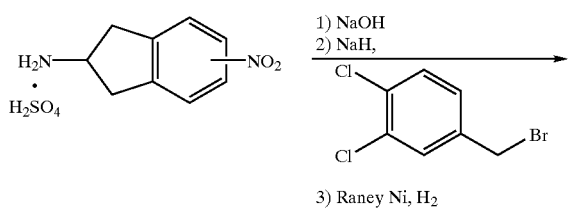

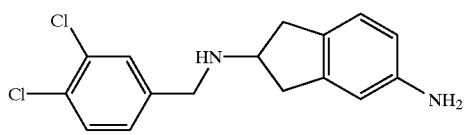

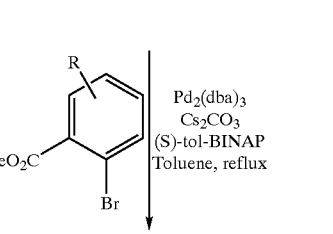
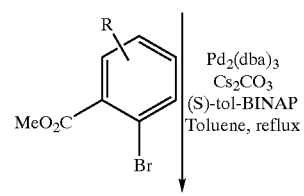

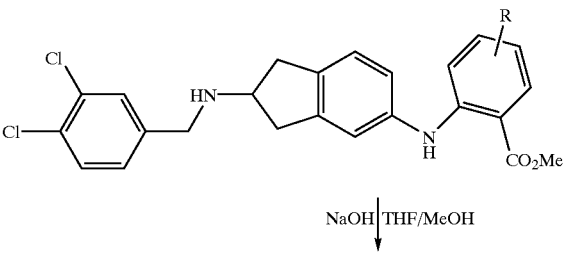

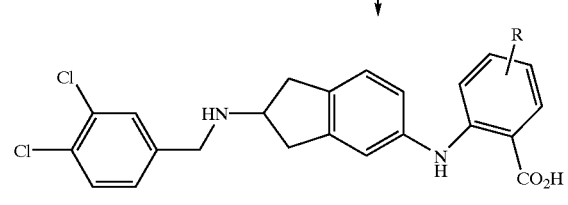

Scheme 3

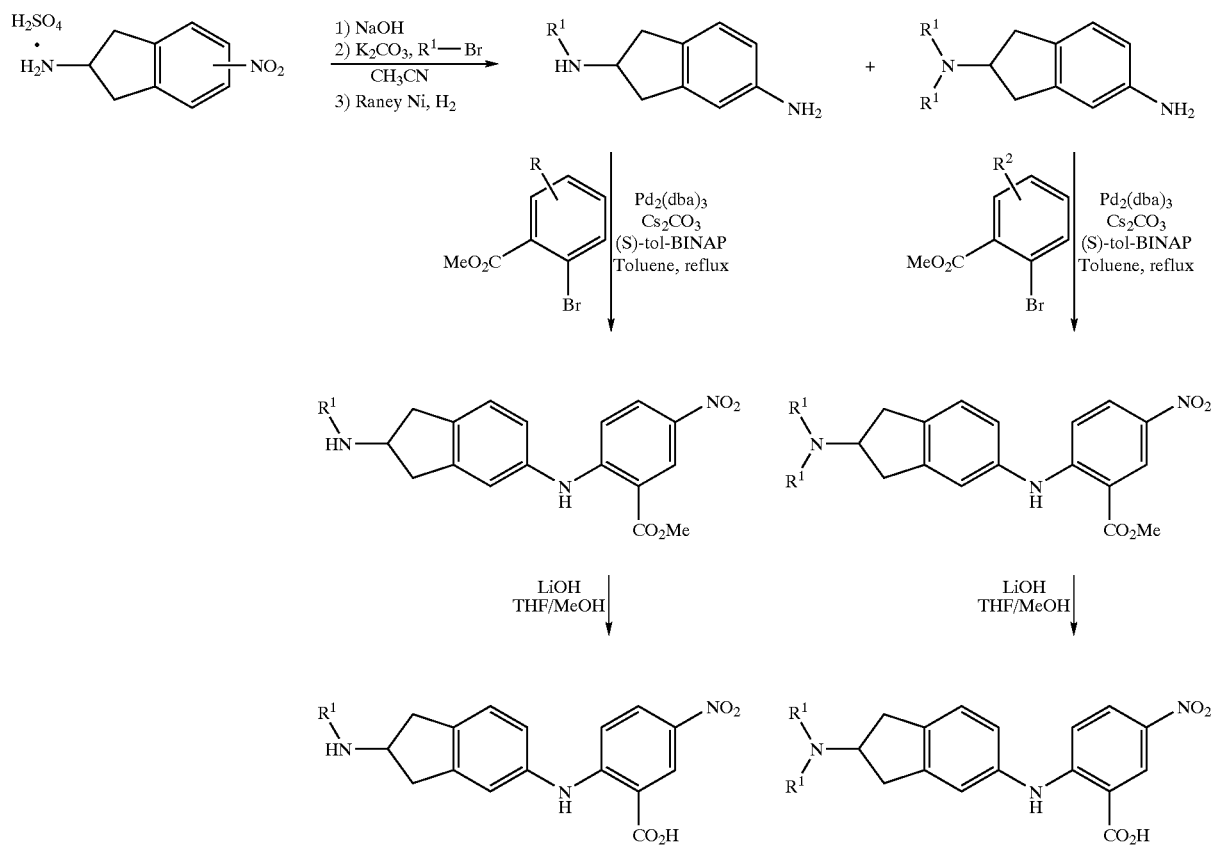

Scheme 4

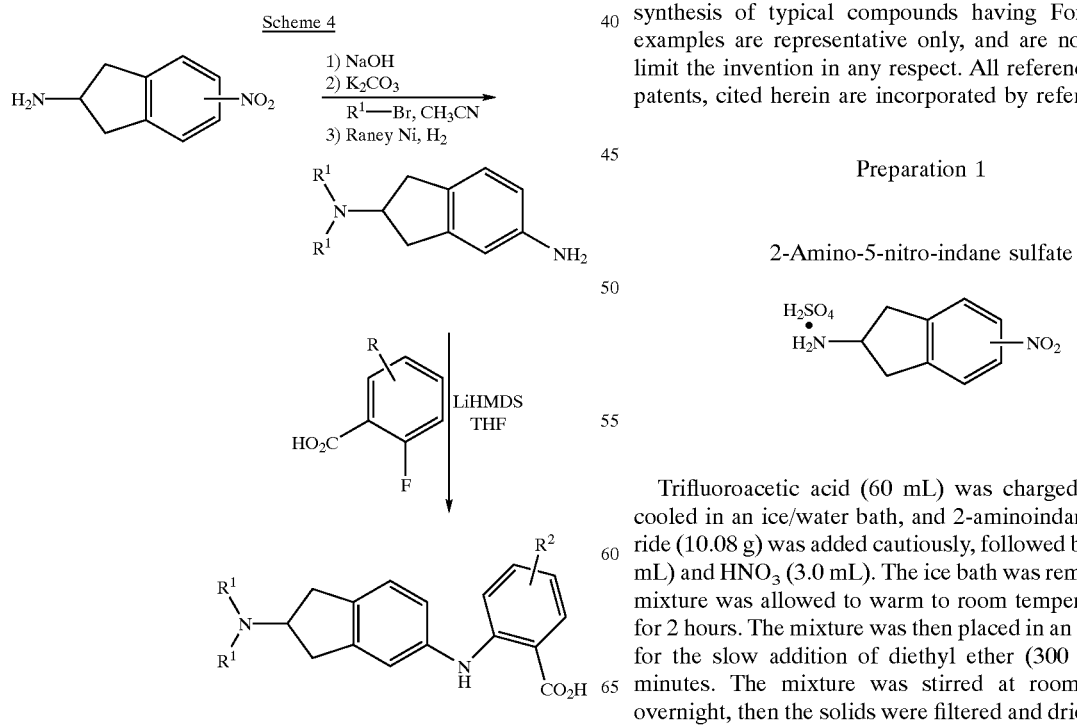

The following detailed examples further illustrate the synthesis of typical compounds having Formula I. The examples are representative only, and are not intended to limit the invention in any respect. All references, including patents, cited herein are incorporated by reference.

Preparation 1

2-Amino-5-nitro-indane sulfate

Trifluoroacetic acid (60 mL) was charged into a flask, cooled in an ice/water bath, and 2-aminoindane hydrochloride (10.08 g) was added cautiously, followed by $H_2SO_4$ (6.0 mL) and $HNO_3$ (3.0 mL). The ice bath was removed, and the mixture was allowed to warm to room temperature and stir for 2 hours. The mixture was then placed in an ice water bath for the slow addition of diethyl ether (300 mL) over 35 minutes. The mixture was stirred at room temperature overnight, then the solids were filtered and dried in vacuo to give 15.43 g of 2-amino-5-nitro-indane sulfate.

Preparation 2

2-(4-Fluorobenzyl)amino-5-nitro-indane and
2-[bis-(4-Fluorobenzyl)amino]-5-nitro-indane

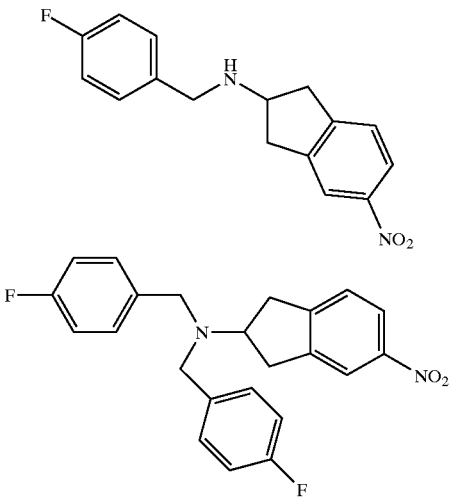

2-Amino-5-nitro-indane sulfate (3 g) from Preparation 1 was dissolved in 10 mL water and 20 mL 2 M NaOH. The mixture was extracted three times with 40 mL methyl t-butyl ether, and the organic layers were combined and dried over MgSO$_4$/Na$_2$SO$_4$, filtered, and concentrated by rotary evaporation. The residual oil was taken up in 30 mL CH$_3$CN, to which 4-fluorobenzyl bromide (2.26 g) was added, followed by K$_2$CO$_3$. The mixture was heated at reflux for 18 hours, cooled to room temperature, filtered, and concentrated. The residual oil was purified by medium pressure liquid column chromatography on silica gel (MPLC, biotage column, solvent gradient 99:1 to 85:15 (CH$_2$Cl$_2$ /1% NH$_4$OH in MeOH). The desired mono-alkylated aminoindane was obtained in 35% yield (1.10 g), and the bis-dialkylated aminoindane was also isolated (1.38 g, 32% yield). MS (APCI) m/z 287 (M$^+$+1) monoalkylated, MS (APCI) m/z 395 (M$^+$+1) dialkylated.

Preparation 3

General Conditions For Reduction of the Nitro Group

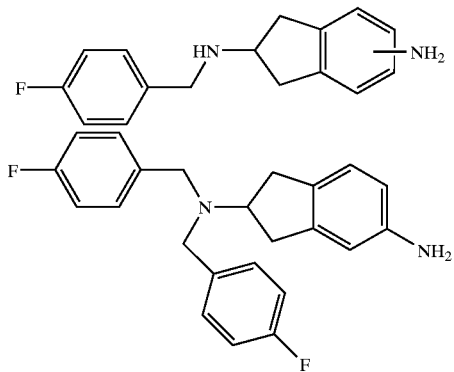

The nitro substituted indanes from Preparation 2 were reacted with hydrogen in the presence of Raney nickel to give the corresponding 2-alkyl and 2-dialkylamino-5-aminoindanes. The 2-amino-5-nitro-indane sulfate from Preparation 1 can be similarly hydrogenated to provide 2,5-diamino-indane.

Preparation 4

2-n-Pentylamino-5-nitro-indane and
2-N,N-di-n-Pentylamino-5-nitro-indane

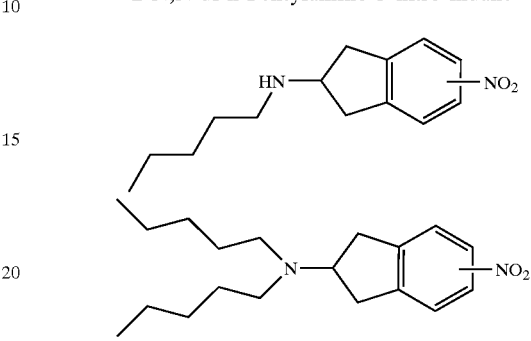

2-Amino-5-nitro-indane sulfate from Preparation 1 (2 g) was dissolved in 20 mL water and brought to pH=11 with 2N NaOH. The aqueous solution was extracted with 3×30 mL methyl t-butyl ether, the organics were combined, dried over MgSO$_4$/Na$_2$SO$_4$, filtered, and concentrated. The residual oil was dissolved in 30 mL acetonitrile, potassium carbonate (1 g) and 1-bromopentane (1.79 mL) were added. The mixture was stirred at reflux for 18 hours, then filtered, concentrated, and purified by column chromatography (MPLC, silica, gradient 1:1 to 3:1 ethyl acetate in hexanes) to give the mono-alkylated amine (0.26 g, 14% yield) and the dialkylated amine (0.99 g, 43% yield). MS mono-alkylated (APCI) m/z 249.1 (M$^+$+1). MS dialkylated (APCI) m/z 319.2 (M$^+$+1).

Preparation 5

2-(3,4-Dichlorobenzyl)amino-5-nitro-indane

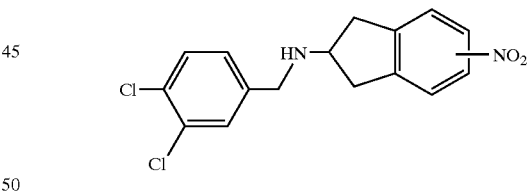

Sulfuric acid (10 mL) was charged into a flask and cooled in an ice/water bath containing 2-amino-5-nitro-indane hydrochloride (1.68 g), followed by HNO$_3$ (0.39 mL). The cooling bath was removed, and the mixture was stirred at room temperature for 30 minutes, and then again cooled in an ice/water bath. Sodium hydroxide (25% soln) was added carefully to pH=11. The solution was then extracted with 4×60 mL diethyl ether. The combined organic layers were filtered through celite, dried over MgSO$_4$/Na$_2$SO$_4$, filtered, and concentrated. The residual black oil was dissolved in THF (25 mL), cooled to 0° C. for the addition of NaH (0.4 g, 60% dispersion in mineral oil). After 5 minutes, dichloro benzyl bromide (3.0 g) was added, and the reaction was stirred at room temperature for 16 hours. The reaction mixture was diluted with 20 mL water and 40 mL Et$_2$O, the layers were separated, and the organics were washed with 20 mL water. The aqueous layers were combined and washed with 30 mL Et$_2$O, and the organic layers were combined, dried over MgSO$_4$/Na$_2$SO$_4$, filtered through celite, and concentrated. The black oil was purified by column chromatography (MPLC, Isco ReadiSep silica column, solvent gradient 80:20 to 50:50 Hexane/EtOAc) to give 2-(3,4-dichlorobenzyl)amino-5-nitro-indane (1.05 g, 32% yield). MS (APCI) m/z 336.1 (M$^+$–1). The nitro indane was reduced by reaction with hydrogen and Raney nickel to give 2-(3,4-dichlorobenzyl)amino-5-amino-indane.

Preparation 6
2-Amino-5-(3,4-dichlorophenylamino)-indane

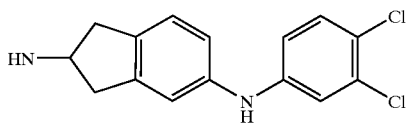

2,5-Diamino-indane (0.77 g) (from Preparation 3) was taken up in toluene (0.25 M), and nitrogen was bubbled through the solution for 5 minutes. (S)-(–)-2,2'-bis(di-p-tolyl-phosphino)-1,1'-binaphthyl [(S)-tol-BINAP] (0.176 g) and palladium dibenzylidene acetone (Pd$_2$(dba)$_3$) (0.123 g), Cs$_2$CO$_3$ (2.37 g) and 3,4-dichloro-1-iodo benzene (1.42 g) was added, and the mixture was heated at reflux for 36 hours. The mixture was then cooled, diluted with diethyl ether, filtered through a plug of celite, concentrated, and purified by medium pressure liquid chromatography (silica gel column, eluted with CH$_2$Cl$_2$/MeOH gradient 1% MeOH to 20% MeOH). The fractions containing any trace of the desired product (mass spec) were combined and concentrated to give 2-amino-5-(3,4-dichlorophenylamino)-indane (0.54 g, 35% yield). MS (APCI) m/z 293.1 (M$^+$+1).

EXAMPLE 1

2-[(2-N,N-di-n-pentylamino)-indan-5-yl]amino-5-nitro-benzoic Acid

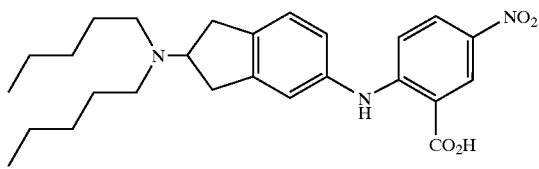

2-N,N-di-n-Pentylamino-5-amino-indane (prepared as described in Preparation 3) (0.88 g) was dissolved in toluene (0.25 M), and nitrogen was bubbled through the solution for 5 minutes. (S)-tol-BINAP (0.16 g) and Pd$_2$(dba)$_2$ (0.073 g), Cs$_2$CO$_3$ (1.39 g), and methyl 1-bromo-4-nitro benzoate (0.66 g) were added, and the mixture was heated at reflux for 18 hours. The mixture was then cooled, diluted with diethyl ether, filtered through a plug of celite, concentrated, and purified by medium pressure liquid chromatography (silica gel column, eluted with CH$_2$Cl$_2$/MeOH gradient 1% MeOH to 10% MeOH). The fractions containing any trace of the desired product (mass spec) were combined and concentrated to give methyl 2-[(2-N,N-di-n-pentylamino)-indane-5-yl]amino-5-nitro-benzoate (1.28 g, 90% yield). MS (APCI) m/z 468.1 (M$^+$+1). The methyl benzoate (0.5 g) was dissolved in 20 mL 1:1 THF/MeOH; this solution was treated with 4 mL 1 M LiOH and stirred at room temperature for 24 hours. When the starting material was no longer observed by mass spec, the mixture was concentrated, and the residual oil was purified by column chromatography (MPLC, silica, gradient 98:2 to 80:20)(CH$_2$Cl$_2$/MeOH+1% NH$_4$OH). Fractions containing the desired product were combined, concentrated, and dried in vacuo overnight to give 2-[(2-N,N-di-n-pentylamino)-indan-5-yl]amino-5-nitro-benzoic acid (0.240 g, 49% yield). MS (APCI) m/z 454.2 (M$^+$+1). CHN for (C$_{26}$H$_{35}$N$_3$O$_4$) calc: C, 68.85, H, 7.78, N, 9.26; found: C, 69.37, H, 7.49, N, 8.91.

EXAMPLE 2

Methyl 2-[2-(3,4-Dichloro-benzylamino)-indan-5-ylamino]-benzoate

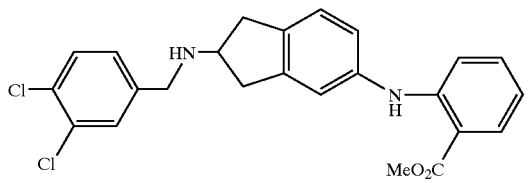

2-(3,4-Dichloro-benzylamino)-5-amino-indane (1.08 g) was dissolved in toluene (0.25 M), and nitrogen was bubbled through the solution for 5 minutes. (S)-tol-BINAP (0.12 g) and Pd$_2$(dba)$_2$ (0.08 g), Cs$_2$CO$_3$ (1.6 g), and methyl 1-bromo benzoate (0.76 g) were added, and the mixture was heated at reflux for 24 hours. The mixture was then cooled, diluted with diethyl ether, filtered through a plug of celite, concentrated, and purified by medium pressure liquid chromatography (silica gel column, eluted with CH$_2$Cl$_2$/MeOH gradient 1% MeOH to 10% MeOH). The fractions containing any trace of the desired product (mass spec) were combined and concentrated to give methyl 2-[2-(3,4-dichloro-benzylamino)-indan-5-ylamino]-benzoate (0.98 g, 63% yield). MS (APCI) m/z 441.2 (M$^+$+1). CHN for (C$_{24}$H$_{22}$Cl$_2$N$_2$O$_2$·0.13CH$_3$OH) calc: C, 65.05, H, 5.09, N, 6.29; found: C, 64.72, H, 4.96, N, 6.35.

EXAMPLE 3

2-[2-(3,4-Dichlorobenzylamino)-indane-5-ylamino]-benzoic acid

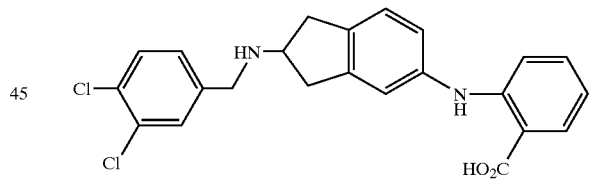

Methyl 2-[2-(3,4-dichloro-benzylamino)-indan-5-ylamino]-benzoate (0.98 g) was dissolved in 20 mL 1:1 THF/MeOH, and this solution was treated with 9 mL 50% NaOH and stirred at room temperature for 24 hours. When the starting material was no longer observed by mass spec, the mixture was concentrated to remove the MeOH, extracted with diethyl ether, and the precipitate was collected by filtration and dried in vacuo overnight to give 2-[2-(3,4-dichlorobenzylamino)-indane-5-ylamino]-benzoic acid (0.09 g, 10% yield). MS (APCI) m/z 427.1 (M++1). CHN for (C$_{23}$H$_{20}$Cl$_2$N$_2$O$_2$·1.85HCl) calc: C, 55.83, H, 4.45, N, 5.66; found: C, 55.45, H, 4.22, N, 5.50.

EXAMPLE 4

2-[2-(3,4-Dichlorobenzylamino)-indan-5-ylamine]-5-nitro-benzoic Acid

By following the procedure of Example 2, 2-(3,4-dichlorobenzylamino)-5-amino-indane was reacted with methyl 2-bromo-5-nitro benzoate to give methyl 2-[2-(3,4-dichlorobenzyl-amino)-indan-5-yl-amino]-5-nitro-benzoate (0.65 g, 69% yield). MS (APCI) m/z 486.0 (M$^+$+1).

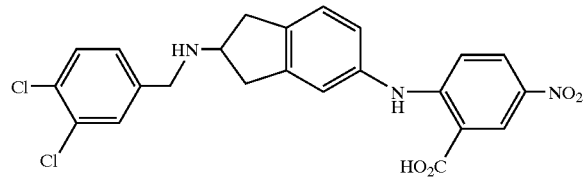

The methyl benzoate (0.65 g) was dissolved in 10 mL 1:1 THF/MeOH, and this solution was treated with 2 mL 50% NaOH and 1 mL water and stirred at room temperature for 18 hours. When the starting material was no longer observed by mass spec, the mixture was concentrated, the solids were dissolved in ethyl acetate/water 1:1. The layers were separated, and the aqueous layer was extracted with 2×20 mL ethyl acetate. The organic layers were combined and washed with 10 mL 50% saturated NaCl, dried over MgSO$_4$/Na$_2$SO$_4$, filtered, and concentrated. The residual oil was purified by column chromatography (MPLC, silica, gradient 98:2 to 80:20)(CH$_2$Cl$_2$/MeOH+1% NH$_4$OH). Fractions containing the desired product were combined, concentrated, and dried in vacuo overnight to give 2-[2-(3,4-dichlorobenzylamino)-indan-5-ylamino]-5-nitro-benzoic acid (0.38 g, 60% yield). MS (APCI) m/z 470.0 (M$^+$−1). CHN for (C$_{23}$H$_{19}$Cl$_2$N$_3$O$_4$·CH$_2$Cl$_2$) calc: C, 55.58, H, 3.94, N, 8.31; found: C, 55.25, H, 3.88, N, 8.32.

EXAMPLE 5

2-[2-(3,4-Dichlorobenzylamino)-indan-5-ylamino]-5-methoxy-benzoic acid

By following the general procedure of Example 2, 2-(3,4-dichlorobenzylamino)-5-amino-indane was reacted with methyl 2-bromo-5-methoxy benzoate to give methyl 2-[2-(3,4-dichlorobenzylamino)-indan-5-ylamino]-5-methoxy-benzoate (0.130 g, 11% yield). MS (APCI) m/z 471.0 (M$^+$+1).

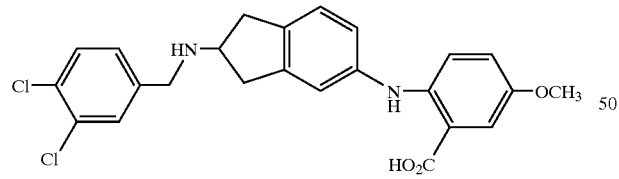

The methyl benzoate (0.130 g) was taken up in 20 mL 1:1 THF/MeOH and was treated with 1 M LIOH (3 mL). The mixture was stirred at room temperature for 48 hours. The mixture was then concentrated, and the residual oil was purified by chromatography (MPLC, silica, gradient 95:5 to 75:25 (CH$_2$Cl$_2$/MeOH). Fractions containing the desired product were combined, concentrated, and dried in vacuo overnight to give 2-[2-(3,4-dichlorobenzylamino)-indan-5-ylamino]-5-methoxy-benzoic acid (0.03 g, 24% yield). MS (APCI) m/z 457.0 (M$^+$+1). CHN for (C$_{24}$H$_{22}$Cl$_2$N$_2$O$_3$·0.6H$_2$O) calc: C, 61.57, H, 4.98, N, 5.98; found: C, 61.23, H, 4.88, N, 5.69.

EXAMPLE 6

2-(2-Dipentylamino-indan-5-yl-amino)-5-methyl-benzoic acid

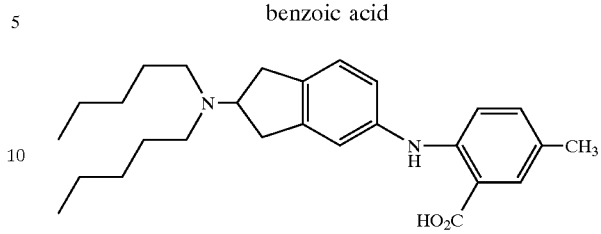

2-(2-Dipentylamino)-5-amino-indane (0.5 g) was taken up in THF (8.7 mL) and cooled to −78° C. for the addition of LiHMDS (4.0 mL, 1 M in THF). 2-Fluoro-5-methyl benzoic acid (0.27 g) was added after 5 minutes, and the cold bath was removed. The mixture was allowed to warm to room temperature and stir for 16 hours. The mixture was diluted with diethyl ether and water. The layers were separated, and the aqueous layer was extracted with 2×20 mL diethyl ether. The organic layers were combined, dried over MgSO$_4$/Na$_2$SO$_4$, filtered, and concentrated. The residual oil was purified by column chromatography (MPLC, silica, gradient 95:5 to 75:25)(CH$_2$Cl$_2$/MeOH). Fractions containing the desired product were combined, concentrated, and dried in vacuo overnight to give 2-(2-dipentylamino-indan-5-yl-amino)-5-methyl-benzoic acid (0.029 g, 4% yield). MS (APCI) m/z 421.2 (M$^+$+1).

EXAMPLE 7

4-(2-Dipentylamino-indan-5-yl-amino)-3-nitro-benzoic Acid

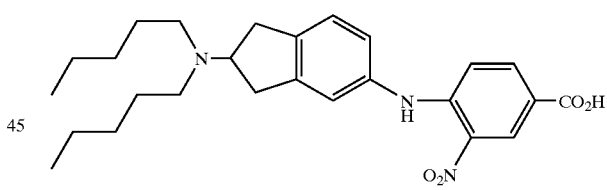

2-(2-Dipentylamino)-5-amino-indane (0.5 g) was taken up in THF (8.7 mL) and cooled to −78° C. for the addition of LiHMDS (4.0 mL, 1 M in THF). 4-Fluoro-3-nitro benzoic acid (0.32 g) was added after 5 minutes, and the cold bath was removed. The mixture was allowed to warm to room temperature and stir for 16 hours. The mixture was diluted with diethyl ether and water. The layers were separated, and the aqueous layer was extracted with 2×20 mL diethyl ether. The organic layers were combined, dried over MgSO$_4$/Na$_2$SO$_4$, filtered, and concentrated. The residual oil was purified by column chromatography (MPLC, silica, gradient 95:5 to 75:25)(CH$_2$Cl$_2$/MeOH). Fractions containing the desired product were combined, concentrated, and dried in vacuo overnight to give 4-(2-dipentylamino-indan-5-yl-amino)-3-nitro-benzoic acid (0.300 g, 38% yield). MS (APCI) m/z 454.1 (M$^+$+1).

EXAMPLE 8

Methyl 2-[5-(3,4-dichlorophenylamino)-indan-2-ylamino]-5-nitro-benzoate

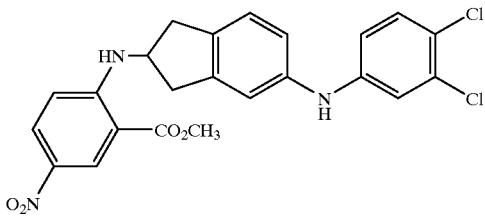

2-Amino-5-(3,4-dichlorophenylamino)-indane (0.20 g) was taken up in toluene (0.25 M), and nitrogen was bubbled through the solution for 5 minutes. (S)-tol-BINAP (0.023 g) and $Pd_2(dba)_2$ (0.05 g), $Cs_2CO_3$ (0.31 g), and methyl 2-bromo-4-nitro benzoate (0.18 g) was added, and the mixture was heated at reflux for 18 hours. The mixture was then cooled, diluted with diethyl ether, filtered through a plug of celite, concentrated, and purified by medium pressure liquid chromatography (silica gel column, eluted with $CH_2Cl_2$/MeOH gradient 1% MeOH to 20% MeOH). The fractions containing any trace of the desired product (mass spec) were combined and concentrated to give methyl 2-[5-(3,4-dichlorophenylamino)-indan-2-ylamino]-5-nitro-benzoate (0.10 g, 26% yield). MS (APCI) m/z 472.0 ($M^+$+1).

EXAMPLE 9

2-[5-(3,4-Dichlorophenylamino)-indan-2-ylamino]-5-nitro-benzoic acid

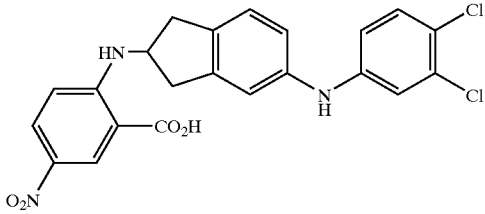

By following the procedure of Example 4, methyl 2-[5-(3,4-dichlorophenylamino)-indan-2-ylamino]-5-nitro-benzoate was reacted with sodium hydroxide in THF/MeOH to give 2-[5-(3,4-dichlorophenylamino)-indan-2-ylamino]-5-nitro-benzoic acid (0.017 g, 18% yield). MS (APCI) m/z 457.9 ($M^+$+1).

EXAMPLE 10

2-[2-(4-Fluorobenzylamino)-indan-5-ylamino]-5-nitro-benzoic acid

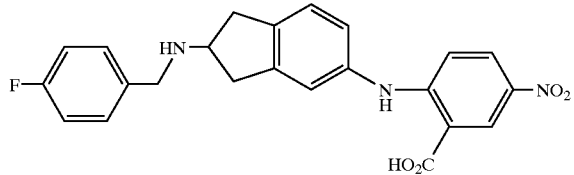

2-(4-Fluorobenzylamino)-5-amino-indane (0.90 g) was taken up in toluene (0.25 M), and nitrogen was bubbled through the solution for 5 minutes. (S)-tol-BINAP (0.18 g) and $Pd_2(dba)_2$ (0.08 g), $Cs_2CO_3$ (1.59 g), and methyl 1-bromo-4-nitro benzoate (0.75 g) were added, and the mixture was heated at reflux for 48 hours. The mixture was then cooled, diluted with diethyl ether, filtered through a plug of celite, concentrated, and partially purified by medium pressure liquid chromatography (silica gel column, eluted with $CH_2Cl_2$/MeOH gradient 1% MeOH to 10% MeOH). The fractions containing any trace of the desired product (mass spec) were combined and concentrated. The residual crude oil was dissolved in 10 mL 1:1 THF:MeOH with 1 mL 2N NaOH, and the reaction mixture was stirred at room temperature 4 hours. When the starting material was no longer observed by mass spec, the mixture was concentrated, and the residual oil was purified by column chromatography (MPLC, silica, gradient 95:5 to 75:25 ($CH_2Cl_2$/1% $NH_4OH$ in MeOH). Fractions containing the desired product were combined, concentrated, and dried in vacuo overnight to give 0.83 g of 2-[2-(4-fluorobenzylamino)-indan-5-ylamino]-5-nitro-benzoic acid. MS (APCI) m/z 422.0 ($M^+$+1). CHN for ($C_{23}H_{20}F_1N_3O_4$·0.68[$H_2O$]) calc: C, 63.70, H, 4.96, N, 9.69; Found: C, 63.32, H, 4.69, N, 9.65.

EXAMPLE 11

2-{2-[bis-(4-Fluorobenzyl)amino]indan-5-ylamino}-5-nitro-benzoic acid

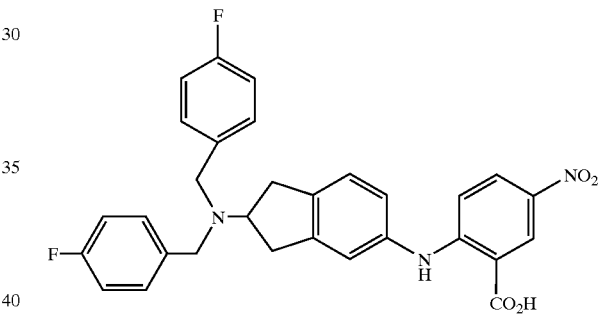

2[bis-(4-Fluorobenzyl)amino]-5-amino-indane (1.28 g) was taken up in toluene (0.25 M), and nitrogen was bubbled through the solution for 5 minutes. (S)-tol-BINAP (0.17 g) and $Pd_2(dba)_2$ (0.12 g), $Cs_2CO_3$ (1.6 g), and methyl 1-bromo-4-nitro benzoate (0.76 g) were added, and the mixture was heated at reflux for 48 hours. The mixture was then cooled, diluted with diethyl ether, filtered through a plug of celite, concentrated, and partially purified by medium pressure liquid chromatography (silica gel column, eluted with $CH_2Cl_2$/MeOH gradient 1% MeOH to 10% MeOH). The fractions containing any trace of the desired product (mass spec) were combined and concentrated to give 1.89 g of the coupled ester. The residual crude oil was dissolved in 30 mL THF, and 20 mL of this solution was treated with 5 mL 2N NaOH and stirred at room temperature for 12 hours. When the starting material was no longer observed by mass spec, the mixture was concentrated, and the residual oil was purified by column chromatography (MPLC, silica, gradient 95:5 to 75:25 ($CH_2Cl_2$/1% $NH_4OH$ in MeOH). Fractions containing the desired product were combined, concentrated, and dried in vacuo overnight to give 0.063 g 2-{2-[bis-(4-fluorobenzyl)amino]indan-5-ylamino}-5-nitro-benzoic acid pure. MS (APCI) m/z 530.0 ($M^+$+1). CHN for ($C_{30}H_{25}F_2N_3O_4$·$CH_3OH$) calc: C, 66.22, H, 5.23, N, 7.46; Found: C, 66.56, H, 5.26, N, 6.97.

EXAMPLE 12

2-[2-(n-Pentylamino)-indan-5-ylamino]-5-nitro-benzoic acid

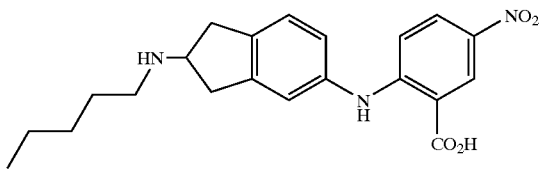

2-n-Pentylamino-5-amino-indane (0.32 g) was taken up in toluene (0.2 M), and nitrogen was bubbled through the solution for 5 minutes. (S)-tol-BINAP (0.076 g) and $Pd_2(dba)_2$ (0.04 g), $Cs_2CO_3$ (0.68 g), and methyl 1-bromo-4-nitro benzoate (0.32 g) were added, and the mixture was heated at reflux for 48 hours. The mixture was then cooled, diluted with diethyl ether, filtered through a plug of celite, concentrated, and partially purified by medium pressure liquid chromatography (silica gel column, eluted with $CH_2Cl_2$/MeOH gradient 1% MeOH to 10% MeOH). The fractions containing any trace of the desired product (mass spec) were combined and concentrated to give 0.42 g of the coupled ester. The residual crude oil was dissolved in 16 mL 1:1 THF/MeOH; this solution was treated with 1 mL 2N NaOH and stirred at room temperature for 12 hours. When the starting material was no longer observed by mass spec, the mixture was concentrated, and the residual oil was purified by column chromatography (MPLC, silica, gradient 98:2 to 80:20 ($CH_2Cl_2$/MeOH). Fractions containing the desired product were combined, concentrated, and dried in vacuo overnight to give 2-[2-(n-pentylamino)-indan-5-ylamino]-5-nitro-benzoic acid (0.170 g, 30% yield). MS (APCI) m/z 382.0 ($M^+$-1). CHN for ($C_{21}H_{25}N_3O_4$·0.35$CH_2Cl_2$) calc: C, 62.06, H, 6.27, N, 10.17; found: C, 61.67, H, 6.34, N, 10.15.

BIOLOGICAL EXAMPLES

Invention compounds of Formula I can be evaluated in several standard in vitro and in vivo assays which are well-established as indicative of clinical usefulness in treating Alzheimer's disease and other conditions associated with amyloid formation.

Amyloid Assays

BASSR (Beta-Amyloid Self-Seeding Radioassay)

An assay for inhibitors of self-seeded amyloid fibril growth

Materials:
Stock Solutions:
Assay Buffer—50 nM sodium phosphate, pH 7.5, 100 mM NaCl, 0.02% $NaN_3$, 1 M urea (filter and store at 4° C.)
Soluble Aβ(1–40) peptide (Bachem, Torrance, Calif.)—2.2 mg/mL in deionized $H_2O$ (stored in aliquots at –20° C., keep on ice when thawed) will self-seed after 1 week storage. Typically, the solution should be stored until no lag phase is seen in the assay.
$^{125}$I-labeled Aβ(1–40)—150 to 350K cpm/μL in 100% acetonitrile—0.1% trifluoroacetic acid (TFA)—1% β-mercaptoethanol (aliquots stored at –20° C.). $^{125}$I-labeled Aβ(1–40) can be made in accordance with the procedure set forth by H. Levine, III in *Neurobiol. Aging*, 16:755 (1995), which is hereby incorporated by reference, or this reagent may be purchased from Amersham, Arlington Heights, Ill. Final assay conditions: 30 μM soluble Aβ(1–40) in deionized water in assay buffer+20 to 50K cpm $^{125}$I-labeled Aβ(1–40) per assay. Compound to be tested is dissolved in dimethylsulfoxide (DMSO), typically 5 to 50 mM stock, such that the final concentration of DMSO is <1% v/v in the assay.

Assay: Reaction mixture for 50 assays (on ice) is comprised of 0.1 to 0.2 μL of $^{125}$I-labeled $A^{125}$I-labeled Aβ(1–40)+1 μL of soluble Aβ(1–40)+13.5 μL assay buffer per assay. The following are the amounts of the components of the reaction mixture sufficient for 50 assay wells.

5 to 10 μL $^{125}$I-labeled Aβ(1–40) dried down
675 μL assay buffer
50 μL soluble Aβ(1–40)

Assay Method
1) Prepare reaction mixture above by mixing components and storing on ice.
2) Pipet 14.5 μL of reaction mixture into each of 50 wells on a polypropylene U-bottom 96-well microtiter plate on ice (Costar 3794).
3) Add 1.7 μL of diluted compound to be tested to each well in a column of eight, including solvent control. Serial 3-fold dilutions from 1 mM (100 μM final) in assay buffer-urea=7 dilutions+zero. Each 96-well plate can therefore accommodate 11 samples+1 Congo Red control (0.039–5 μM final in 2-fold steps).
4) Seal the plate with aluminum film (Beckman 538619) and incubate for 10 minutes on ice.
5) Raise the temperature to 37° C. and incubate for 3 to 5 hours (depending on the lot of the peptide).
6) Remove the aluminum film and add 200 μL/well of ice cold assay buffer with urea, collecting the radiolabeled fibrils by vacuum filtration through 0.2-μm pore size GVWP filters in 96-well plates (Millipore MAGV N22, Bedford, Mass.). Determine the radioactivity of the filters using standard methods well-known to those skilled in the art.

BASST (Beta-Amyloid Self-Seeding, Thioflavin T)
An assay for inhibitors of self-seeded amyloid fibril growth
Methods:
Materials:
Stock Solutions:
Assay Buffer—50 mM sodium phosphate, pH 7.5, 100 mM NaCl, 0.02% $NaN_3$, 1 M urea (filter and store at 4° C.)
Soluble Aβ(1–40)—2.2 mg/mL in deionized $H_2O$ (store in aliquots at –20° C., keep on ice when thawed) will self-seed after 1 week storage. Typically, the solution should be stored until no lag phase is seen in the assay.
Final assay conditions: 30 μM soluble Aβ(1–40) in deionized water in assay buffer. Compound to be tested is dissolved in DMSO, typically 5 to 50 mM stock, such that the final concentration of DMSO is <1% v/v in the assay.
Assay: Reaction mixture for 50 assays (on ice) comprised of 1 μL of soluble Aβ(1–40)+13.5 μL assay buffer per assay. The following are the amounts of the components of the reaction mixture that result in each of the 50 assay wells.

50 μL soluble Aβ(1–40)
675 μL assay buffer

Assay Method
1) Prepare the reaction mix above by mixing the components and storing on ice.
2) Pipet 14.5 μL of reaction mixture into each of 50 wells of a polystyrene U-bottom 96-well microtiter plate (Corning 25881-96) on ice.
3) Add 1.7 μL of diluted compound to be tested to each well in a column of eight, including solvent control. Serial 3-fold dilutions from 1 mM (100 μM final) in assay buffer-urea=7 dilutions+zero. Each 96-well plate can therefore accommodate 11 samples+1 Congo Red control (0.039–5 µM final in 2-fold steps).

4) Seal the plate with aluminum film and incubate for 10 minutes on ice.
5) Raise the temperature to 37° C. and incubate for 3 to 5 hours (depends on the lot of the peptide).
6) Remove the aluminum film and add 250 µL/well of 5 µM thioflavin T (ThT) [T-3516, Sigma-Aldrich] in 50 mM glycine-NaOH, pH 8.5. Read fluorescence on a plate reader (ex=440 nm/20 nm; em=485 nm/20 nm) within 5 minutes.

BAPA (Beta-Amyloid Peptide Aggregation)

This assay is used to provide a measure of inhibition by a compound against the aggregation behavior of the β-amyloid peptide.

The purpose of this assay is to provide a higher volume method of assaying the amount of β-amyloid aggregation using an endpoint assay based on filtration. In this assay, hexafluoroisopropanol (HFIP) is used to break down the initial amyloid peptide to a monomer state and use a concentration of 33 µM which is high enough so that aggregation will occur at pH 6.0 in several hours.

Methods:

Beta-Amyloid Peptide Aggregation, pH 6.0 (BAPA)

In a 96-well plate (Costar 3794), we add 25 µL 50 mM phosphate buffer, pH 6.0, 10 µL 0.5 mg/mL Aβ (1–40) peptide in 20% HFIP+0.1 µL/assay radioiodinated $^{125}$I Aβ (1–40) [$^{125}$I Aβ(1–40)], and 1 µL of the compound to be tested starting at 50 mM with a concentration of DMSO<1%. Then, we incubate for 2 to 4 hours at room temperature. We stop the reaction with 200 µL of 50 mM phosphate buffer, pH 6.0, and filter it through a 0.2 µm 96-well filter plate (Millipore MAGU N22). We wash the filter plate with 100 µL of the same phosphate buffer. Aggregation was detected on a Microbeta counter after impregnating the filters with Meltilex (1450-441) and is corrected for background.

Batym Assay

Methods:

Required Aβ (1–42) (California Peptide) was dried from its HFIP stock solution. The Aβ (1–42) was dissolved in DMSO and then mixed with phosphate buffered saline (PBS) (pH 7.4). The mixed Aβ (1–42) solution was filtered with a Omnipore membrane 0.2-µm syringe filter (Millipore, Bedford, Mass.). The compound to be tested in DMSO (50× concentrate) was put into each well (0.5 µL/well) of a 96-well plate. The Aβ (1–42) solution was added into each well (24.5 µL/well). The plate was centrifuged at 1,000 g for 5 minutes and incubated at 37° C. for 1 day (Aβ1–42; final concentration 100 µM).

After incubation, Thioflavin T (ThT) (30 µM) solution in glycine-NaOH buffer (pH 8.5, 50 mM) was added into each well (250 µL/well), fluorescence was measured (ex=440/20 nm; em=485/20 nm) using a fluorescence plate reader. The inhibitory activity was calculated as the reduction of fluorescence with the following formula:

$$\text{Inhibition (\%)} = \{(F(A\beta) - F(A\beta + \text{compound})) / (F(A\beta) - F(\text{solvent} + \text{compound}))\} \times 100$$

The $IC_{50}$s were calculated by a curve fitting program using the following equation. The data were obtained from two different experiments in triplicate.

$$\text{Inhibition } (x) = 100 - 100 / \{1 + (x/IC_{50})^n\}.$$

x=concentration of tested compound (M).
$IC_{50}$=(M).
n=Hill coefficient.

Representative compounds of Formula I have exhibited inhibitory activities ($IC_{50}$) ranging from about 0.1 to >100 µM in the foregoing assays. The results of these assays for specific representative compounds of the present invention are shown in the table below.

| | Amyloid Inhibition | | | |
|---|---|---|---|---|
| Example No. | BASST $IC_{50}$ µM | BAYTM $IC_{50}$ µM | BASSR $IC_{50}$ µM | BAPA $IC_{50}$ µM |
| 1 | 40 | >100 | >100, >100, >100 | 33 |
| 3 | 40 | >100 | >100 | |
| 4 | 1.1 | 16 | >100, >100, 7.5, 8, 9 | 28 |
| 5 | 30 | >100 | >100, >100, 30 (ppt), 100 | 165 |
| 6 | 21, >100 | >100 (2x) | >100 (5x) | 118 |
| 7 | 8 | >100 | >100, >100, 15, >100 | 118 |
| 9 | 0.25 | | >100, 8 (v), 7 (v), 6 (ppt) | 5 |
| 10 | 30 | 53.8 | >100, >100, 90, 10 | >100 |
| 11 | 1 | 7, 12 | >100, 20 (ppt), 1.2 (ppt), >100 | 7 |
| 12 | >100 | >100 | >100, >100 | 5 |

The invention compounds can also be evaluated in standard in vivo assays commonly used to evaluate agents to treat conditions associated with amyloid aggregation such as Alzheimer's disease. In one assay, amyloid protein is induced into the spleen of mice by subcutaneous injections of silver nitrate, Freund's complete adjuvant, and an intravenous injection of amyloid enhancing factor. Silver nitrate is administered each day through Day 11. Test compounds are administered to the mice daily starting on Day 1 through Day 11. On Day 12, the animals are sacrificed, and the spleens are removed, histologically prepared, stained with Congo red, and the percent area of the spleen occupied by birefringent, Congo red-stained amyloid is quantitated microscopically. Invention compounds will inhibit splenic amyloid deposition.

Another in vivo assay in which the invention compounds can be evaluated uses transgenic mice. The mice bear a human β-amyloid precursor protein transgene with a prion promoter, as descried by Hsiao et al., "Correlative memory deficits, Aβ elevation, and amyloid plaques in transgenic mice," Science 1996;274:99–102. These transgenic mice develop β-amyloid deposits at about 9 months of age. By 15 months, diffuse and compact senile plaques are abundant, primarily in the neocortex, olfactory bulb, and hippocampus. Invention compounds are administered orally to the mice beginning at the age of 8 months (just prior to the onset of amyloid deposits) and continuing for several months (up to about age 14–18 months). The animals are then sacrificed, and the brains are removed. The amount of amyloid in the brain is quantitated both histologically and biochemically. Invention compounds will inhibit amyloid accumulation in the cortex and hippocampus of the test animals.

The foregoing data establish that invention compounds of Formula I are potent inhibitors of protein aggregation, and are thus useful in treating diseases associated with amyloid deposits and to image amyloid deposits for diagnostic use. The compounds typically will be used in the form of pharmaceutical formulations for therapeutic use, and the following examples further illustrate typical compositions.

EXAMPLE 13

Tablet Formulation

| Ingredient | Amount |
| --- | --- |
| Compound of Example 1 | 50 mg |
| Lactose | 80 mg |
| Cornstarch (for mix) | 10 mg |
| Cornstarch (for paste) | 8 mg |
| Magnesium Stearate (1%) | 2 mg |
| | 150 mg |

The compound of Example 1 is mixed with the lactose and cornstarch (for mix) and blended to uniformity to a powder. The cornstarch (for paste) is suspended in 6 mL of water and heated with stirring to form a paste. The paste is added to the mixed powder, and the mixture is granulated. The wet granules are passed through a No. 8 hard screen and dried at 50° C. The mixture is lubricated with 1% magnesium stearate and compressed into a tablet. The tablets are administered to a patient at the rate of 1 to 4 each day for prevention of amyloid and treatment of Alzheimer's disease.

EXAMPLE 14

Parenteral Solution

In a solution of 700 mL of propylene glycol and 200 mL of water for injection is added 20.0 g of compound of Example 9. The mixture is stirred, and the pH is adjusted to 5.5 with hydrochloric acid. The volume is adjusted to 1000 mL with water for injection. The solution is sterilized, filled into 5.0 mL ampoules, each containing 2.0 mL (40 mg of compound of Example 9), and sealed under nitrogen. The 10 solution is administered by injection to a patient suffering from medullary carcinoma of the thyroid and in need of treatment.

EXAMPLE 15

Patch Formulation

Ten milligrams of 2-[2-(3,4-dichlorobenzylamino)-indan-5-yl-amino]-benzoic acid is mixed with 1 mL of propylene glycol and 2 mg of acrylic-based polymer adhesive containing a resinous cross-linking agent. The mixture is applied to an impermeable backing (30 cm²) and applied to the upper back of a patient for sustained release treatment of amyloid polyneuropathy.

The invention and the manner and process of making and using it are now described in such full, clear, concise, and exact terms as to enable any person killed in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:
1. A compound of the Formula I

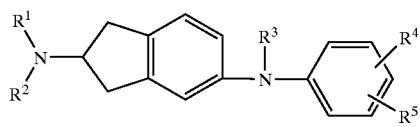

wherein:

$R^1$ and $R^2$ independently are hydrogen, $C_1$–$C_3$ alkyl, $C_2$–$C_8$ alkenyl, $C_2$–$C_8$ alkynyl, $(CH_2)_n$phenyl or $(CH_2)_n$ substituted phenyl, provided that one of $R^1$ and $R^2$ is other than hydrogen;

$R^4$ and $R^5$ independently are hydrogen, halo, $C_1$–$C_8$ alkyl, $C_2$–$C_8$ alkenyl, $C_2$–$C_8$ alkynyl, $(CH_2)_n$phenyl, $(CH_2)_n$ substituted phenyl, $NO_2$, CN, $CF_3$, $C_1$–$C_8$ alkoxy, $CO_2R^6$, tetrazolyl, $NH(C_1$–$C_8$ alkyl), $N(C_1$–$C_8$ alkyl)$_2$, or $SO_2R^6$;

$R^3$ is hydrogen or $C_1$–$C_8$ alkyl;

$R^6$ is hydrogen, $C_1$–$C_8$ alkyl, or $(CH_2)_n$phenyl or $(CH_2)_n$ substituted phenyl;

n is an integer from 0 to 4 inclusive;

or a pharmaceutically acceptable salt, ester, or amide thereof.

2. A compound of claim 1 having Formula II.

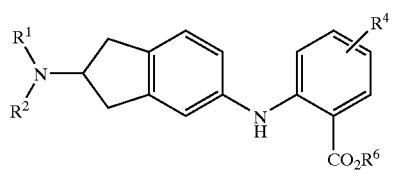

3. A compound of claim 2 wherein $R^6$ is hydrogen.
4. A compound of claim 1 having Formula III

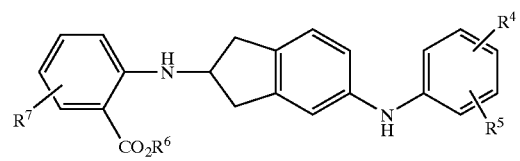

wherein $R^7$ is hydrogen, halo, $NO_2$, CN, $C_1$–$C_8$ alkyl, $C_1$–$C_8$ alkoxy, $CF_3$, $NH_2$, $NH(C_1$–$C_8$ alkyl), or $N(C_1$–$C_8$ alkyl)$_2$.

5. A compound selected from the group consisting of
2-[(2-N,N-di-n-pentylamino)-indan-5-yl]amino-5-nitrobenzoic acid;
Methyl 2-[2-(3,4-Dichloro-benzylamino)-indan-5-ylamino]-benzoate;
2-[2-(3,4-Dichlorobenzylamino)-indane-5-ylamino]-benzoic acid;
2-[2-(3,4-Dichlorobenzylamino)-indan-5-ylamine]-5-nitro-benzoic acid;
2-[2-(3,4-Dichlorobenzylamino)-indan-5-ylamino]-5-methoxy-benzoic acid;
2-(2-Dipentylamino-indan-5-yl-amino)-5-methyl-benzoic acid;
4-(2-Dipentylamino-indan-5-yl-amino)-3-nitro-benzoic acid;

Methyl 2-[5-(3,4-dichlorophenylamino)-indan-2-ylamino]-5-nitro-benzoate;

2-[5-(3,4-Dichlorophenylamino)-indan-2-ylamino]-5-nitro-benzoic acid;

2-[2-(4-Fluorobenzylamino)-indan-5-ylamino]-5-nitro-benzoic acid;

2-{2-[bis-(4-Fluorobenzyl)amino]indan-5-ylamino}-5-nitro-benzoic acid; and

2-[2-(n-Pentylamino)-indan-5-ylamino]-5-nitro-benzoic acid.

6. A method of inhibiting the aggregation of amyloid proteins to form amyloid deposits, the method comprising administering to a patient in need of inhibition of amyloid protein aggregation an amyloid protein aggregation inhibiting amount of a compound of claim 1.

7. A method of inhibiting the aggregation of amyloid proteins to form amyloid deposits, the method comprising administering to a patient in need of inhibition of amyloid protein aggregation an amyloid protein aggregation inhibiting amount of a compound of claim 2.

8. A method of inhibiting the aggregation of amyloid proteins to form amyloid deposits, the method comprising administering to a patient in need of inhibition of amyloid protein aggregation an amyloid protein aggregation inhibiting amount of a compound of claim 3.

9. A pharmaceutical composition comprising a compound of claim 1 together with an excipient, diluent, or carrier therefore.

10. A pharmaceutical composition comprising a compound of claim 2 together with an excipient, diluent, or carrier therefore.

11. A pharmaceutical composition comprising a compound of claim 3 together with an excipient, diluent, or carrier therefore.

12. A pharmaceutical composition comprising a compound of claim 4 together with an excipient, diluent, or carrier therefore.

* * * * *